United States Patent
Ariola et al.

[11] Patent Number: 5,759,175
[45] Date of Patent: Jun. 2, 1998

[54] INTRA-AORTIC BALLOON CATHETER

[75] Inventors: John Ariola, Norton; Kevin R. Heath, Weston, both of Mass.

[73] Assignee: Boston Scientific Corporation, Natick, Mass.

[21] Appl. No.: 819,879

[22] Filed: Mar. 18, 1997

Related U.S. Application Data

[63] Continuation of Ser. No. 556,533, Nov. 13, 1995, abandoned.

[51] Int. Cl.⁶ .................................................. A61M 29/00
[52] U.S. Cl. ................................................................ 604/96
[58] Field of Search ............................. 604/96, 101, 264, 604/280; 606/191, 192, 193–199

[56] References Cited

U.S. PATENT DOCUMENTS

| | | | |
|---|---|---|---|
| 4,327,709 | 5/1982 | Hanson et al. | 128/1 D |
| 4,362,150 | 12/1982 | Lombardi, Jr. et al. | 128/1 D |
| 4,569,332 | 2/1986 | Schiff et al. | 128/1 D |
| 4,646,719 | 3/1987 | Neuman et al. | 128/1 D |
| 4,955,384 | 9/1990 | Taylor et al. | 128/657 |
| 4,994,018 | 2/1991 | Saper | 600/18 |
| 5,090,957 | 2/1992 | Moutafis et al. | 604/96 |
| 5,116,305 | 5/1992 | Milder et al. | 600/18 |
| 5,243,996 | 9/1993 | Hall | 128/772 |
| 5,308,319 | 5/1994 | Ide et al. | 600/18 |
| 5,341,818 | 8/1994 | Abrams et al. | 128/772 |
| 5,346,505 | 9/1994 | Leopold | 606/194 |
| 5,397,306 | 3/1995 | Nobuyoshi et al. | 604/96 |
| 5,411,476 | 5/1995 | Abrams et al. | 604/95 |
| 5,439,443 | 8/1995 | Miyata et al. | 604/96 |
| 5,441,489 | 8/1995 | Utsumi et al. | 604/280 |
| 5,449,343 | 9/1995 | Samson et al. | 604/96 |
| 5,456,665 | 10/1995 | Postell et al. | 604/96 |
| 5,460,607 | 10/1995 | Miyata et al. | 604/96 |
| 5,480,383 | 1/1996 | Bagaoisan et al. | 604/96 |
| 5,505,699 | 4/1996 | Forman et al. | 604/96 |
| 5,507,766 | 4/1996 | Kugo et al. | 606/194 |

FOREIGN PATENT DOCUMENTS

WO 93/17750  9/1993  WIPO.

Primary Examiner—Michael Buiz
Assistant Examiner—Manuel Mendez
Attorney, Agent, or Firm—Crompton, Seager & Tufte, LLC

[57] ABSTRACT

An improved intra-aortic balloon catheter having an outer tube of a polymeric material and an inner tube of superelastic metal material with varying flexibility. The inner tube has a proximal end and a distal end. The inner tube is more flexible proximate the distal end than the proximal end.

16 Claims, 2 Drawing Sheets

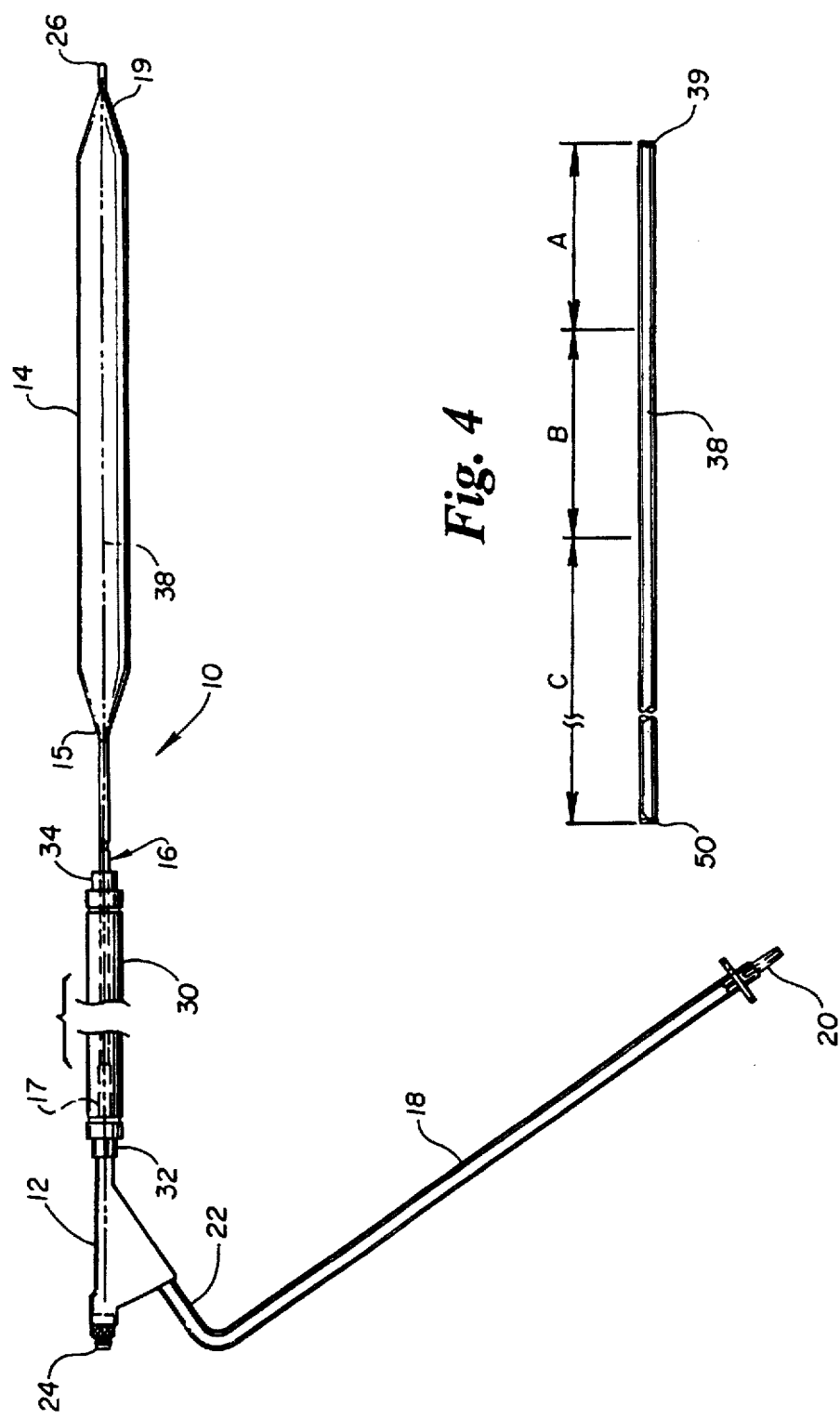

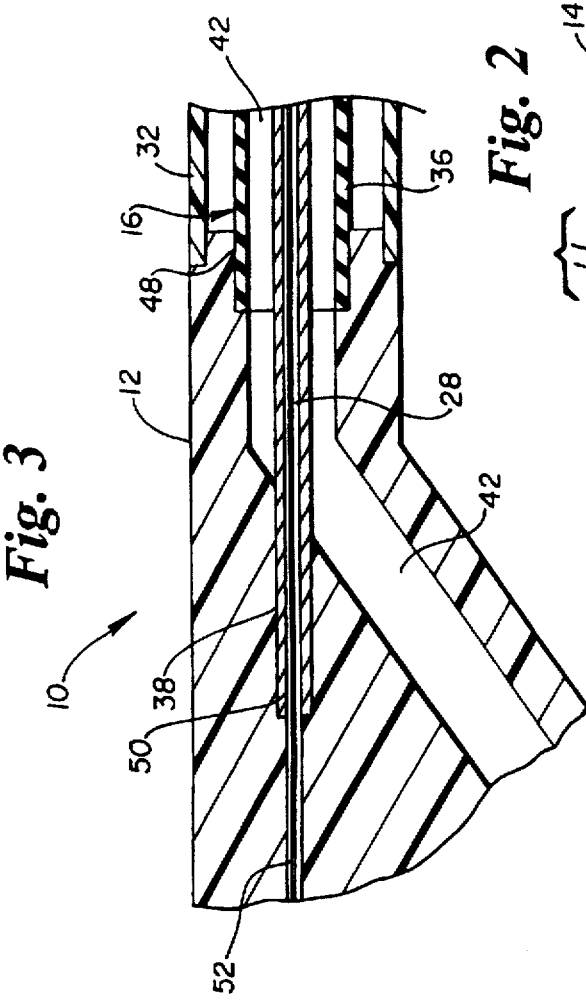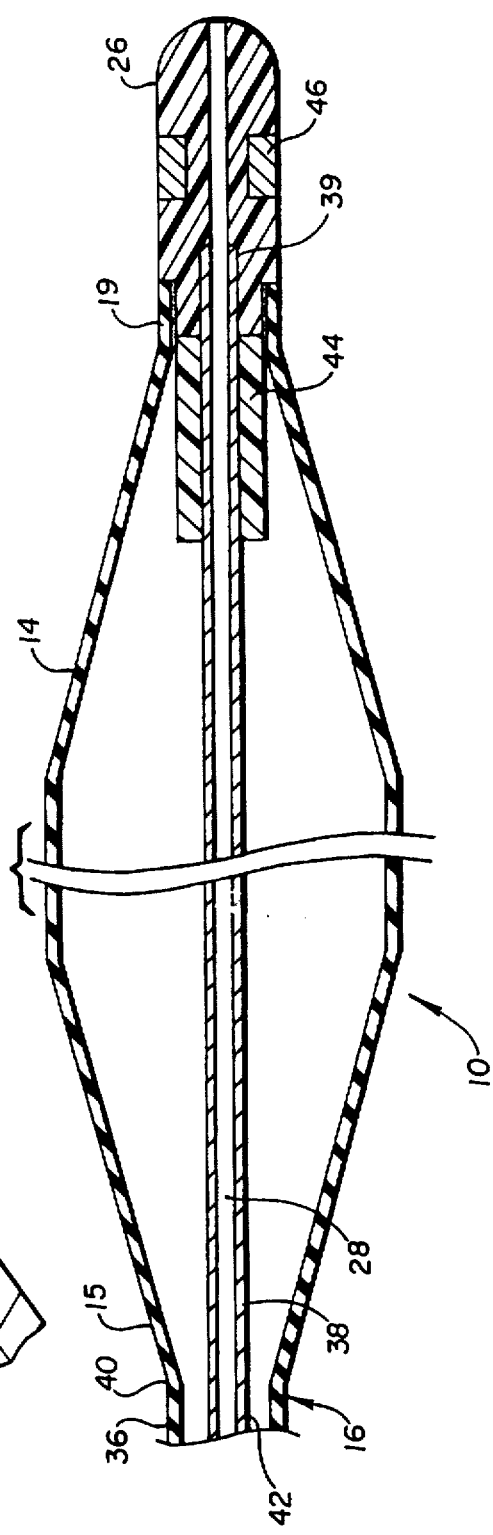

INTRA-AORTIC BALLOON CATHETER

This is a continuation of application Ser. No. 08/556,533 filed on Nov. 13, 1995, entitled "Intra-Aortic Balloon Catheter" now abandoned.

FIELD OF THE INVENTION

The present invention generally relates to the field of intravascular medicine, and more particularly to the field of catheters such as intra-aortic balloon catheters used for assisting the pumping action of the heart.

BACKGROUND OF THE INVENTION

The use of balloon catheters for treatment in the vascular system of the body is well known in the field of medicine. Intra-aortic balloon catheters are used in applications where a patient's heart requires assistance to circulate blood through such patient's vasculature.

Over-the-wire intra-aortic balloon catheters have become a widely used type of intra-aortic balloon catheter. Over-the-wire balloon catheters are generally dual-lumen balloon catheters, including a shaft hanging an inner tube extending longitudinally from the proximal to the distal end of the catheter. The inner tube defines a guidewire lumen also extending longitudinally from the proximal to the distal end of the catheter to facilitate movement of the catheter over a guidewire. An inflatable/deflatable balloon is positioned such that its distal end is sealably attached to the distal end of the inner tube. The shaft of the intra-aortic balloon catheter also includes an outer tube extending longitudinally from the proximal end of the catheter to the proximal end of the balloon where it is sealably attached. The inner tube is generally coaxially disposed within the outer tube to define a fluid flow lumen or gas lumen therebetween from the proximal end of the catheter to the interior of the balloon. A hub assembly is sealably attached to the proximal end of the shaft to provide means for supplying fluid pressure to the balloon through the gas lumen from an external pump. Generally, intra-aortic balloon catheters are constructed of polymeric balloon materials, such as a polyurethane balloon and outer tube, and a polymeric, stainless steel, or metal alloy inner tube.

In operation, the intra-aortic balloon catheter is usually introduced percutaneously into the femoral artery over a guidewire, and advanced through the vasculature until the distal tip of the balloon is positioned just below or distal to the left subclavian artery. Care must be taken during insertion to avoid any trauma or perforation, particularly when the balloon is passing the branches, arteries or curves of the vasculature. Once in position, a balloon pump can be operated synchronously with the patient's heart beat. In particular, the balloon can be inflated and deflated to assist blood circulation from the heart by causing inflation to occur as the aortic valve is closing, and causing deflation to occur just prior to the onset of systole.

It is often difficult to advance a balloon assembly over a guidewire for any great distance. Prior art designs which utilized plastic inner tubes are very flexible, but have poor circumferential rigidity. Typically, thick plastic walls were required to provide adequate compressive strength to obtain sufficient pushability. However, using thick-walled inner tubes results in a reduction in the gas lumen cross-sectional area for an outer tube of a given inside diameter. The reduction in cross-sectional area undesirably slowed deflation and inflation of the balloon. Metal ribbon wrapped plastic inner lumens can also be used, but the added thickness of the metal wrap reduces the available gas lumen area.

Metallic inner tubes have also been utilized. For example, stainless steel inner tubes are relatively less flexible than plastic tubes, but due to the rigidity of stainless steel tubes, they do not as easily track a guidewire. In addition, stainless steel inner tubes are susceptible to kinking at a relatively large kink radius. Superelastic metal alloy inner tubes can also be utilized to provide the finished catheter with a somewhat higher flexibility or steerability than stainless steel versions. Superelastic metal alloy tubes can also have greater pushability than plastic inner tubes having the same wall thickness.

One example of an intra-aortic balloon catheter having a superelastic metal alloy inner tube is disclosed in U.S. Pat. No. 5,456,665 to Postell et al., the disclosure of which is incorporated herein by reference. This catheter comprises a metal alloy inner tube which has uniform longitudinal flexibility. The metal alloy inner tube can be comprised of nitinol, which allows the inner tube to be more kink-resistant than those made from stainless steel, and thinner than those formed from plastic or metal ribbon wrapped plastic.

The inner tube construction of Postell et al. does not provide a tube having varying flexibility along its length. Consequently, the proximal end of the inner tube will be as flexible as the distal end of the tube. It is preferable, however, that the proximal end of the inner tube be more rigid than the extreme distal end of the inner tube. Such a variation in flexibility would provide high pushability along the majority of the length of the catheter, and high flexibility or steerability at the distal end of the catheter which must negotiate the vasculature tracking the guidewire.

SUMMARY OF THE INVENTION

The present invention relates to an improved intra-aortic balloon catheter having an outer tube and an inner tube. The inner tube is constructed utilizing kink-resistant superelastic metal material having varying flexibility of the length thereof and a high degree of pushability. The inner tube is most flexible nearest its distal tip. The flexible tip improves the steerability of the catheter and reduces the likelihood of vessel trauma during placement. The flexibility of the tip end of the improved intra-aortic balloon catheter inner tube can be designed to approach that of prior plastic inner tubes, while the proximal end can have the pushability of prior catheters having metallic inner tubes.

Although reference throughout this specification may be specifically made to intra-aortic balloon catheters, these references are applicable to other catheter types such as guide catheters, diagnostic catheters, coronary, neuro, general periphery, and vascular type catheters.

The present invention provides a dual-lumen intra-aortic balloon catheter design which includes a shaft having an inner tube extending longitudinally from the proximal to the distal end of the catheter. The inner tube defines a guidewire lumen designed to accommodate a guidewire to facilitate placement of the catheter. The inner tube is formed of a highly elastic, kink-resistant metal material such as nitinol having varying flexibility and a high degree of pushability. The inner tube is more flexible nearest its tip.

An inflatable/deflatable balloon is positioned such that the distal end of the balloon is sealably attached to the inner tube proximate its distal end. The shaft of the intra-aortic balloon catheter of the present invention also includes an outer tube extending longitudinally from the proximal end of the catheter to the proximal end of the balloon where it is sealably attached. The outer tube and balloon can preferably be constructed of a polyurethane.

The inner tube is coaxially disposed within the outer tube defining a fluid flow or gas lumen therebetween. A hub assembly is sealably attached to the proximal end of the shaft to provide means for supplying fluid pressure to the balloon through the gas lumen.

In a preferred embodiment, the inner tube is comprised of three regions of flexibility over its longitudinal length, a high flexibility region distal, a transition region intermediate, and a low flexibility region proximal. The inner tube is preferably formed of a kink-resistant, superelastic metal material such as nitinol.

A method of forming the three regions of flexibility of the inner tube is also provided. According to this method, the inner tube is manufactured from nitinol and the three regions of flexibility are formed by selective heat treatment of the inner tube in a high temperature salt bath. The method includes the steps of providing a nitinol tube having a predetermined austinite finish temperature as a starting material. A salt bath is then heated to a desired temperature. The nitinol tube is then dipped in the salt bath such that two of the three regions are submerged. The process of heating the nitinol tube raises its austinite finish temperature, and through a physical change in its material properties, the flexibility of the nitinol tube is increased. Since the third region is not submerged it will retain its original austinite finish temperature. The tube is then extracted slowly at a predetermined rate from the salt bath until only one region is submerged. After continued heat treatment of this single region to a desired austinite finish temperature, the nitinol tube is then removed from the salt bath.

In an alternative version of the method of the present invention, the entire nitinol tube is initially submerged in the salt bath to achieve an overall desired austinite finish temperature. The tube is then removed, then reinserted and extracted slowly from the salt bath following the process described above until only the third region is submerged. In yet another alternative version of the method of the present invention, the entire nitinol tube is alternately held, then extracted at desired rates from the salt bath to create any desired number of austinite finish temperature transition regions and constant temperature regions along the length of the inner tube.

BRIEF DESCRIPTION OF THE DRAWINGS

FIG. 1 is a schematic elevational view of the intra-aortic balloon catheter assembly of the present invention;

FIG. 2 is a simplified partial cross-sectional view of the intra-aortic balloon catheter assembly of FIG. 1 showing the balloon assembly;

FIG. 3 is a simplified partial cross-sectional view of the intra-aortic balloon catheter assembly of FIG. 1 showing the hub assembly; and FIG. 4 is an elevational view of the inner tube of the intra-aortic balloon catheter assembly of FIG. 1 having varying flexibility zones depicted thereon.

DETAILED DESCRIPTION OF THE PREFERRED EMBODIMENTS

Referring now to the drawings, wherein like reference numerals refer to like elements throughout the several views, FIG. 1 shows an elevational view of the intra-aortic balloon catheter 10 in accordance with the present invention. Catheter 10 includes a hub 12, a balloon 14 and a shaft 16 extending therebetween. A strain relief 17 can provide a transition in flexibility between hub 12 and shaft 16. Balloon 14 has a proximal end 15 and a distal end 19. A gas input and output tube 18 includes a proximal end 20 configured for connection to a balloon inflation/deflation pump and a distal end 22 connected to hub 12. Catheter 10 has a proximal end 24 and a distal end including a distal tip member 26. Proximal end 24 includes a fixture defining the proximal end of an inner tube 38 having guidewire lumen 28 (shown in FIGS. 2 and 3). Guidewire lumen 28 extends longitudinally through catheter 10.

Catheter 10 can include a repositioning shield 30 having a proximal end 32 connected to hub 12 and a distal end 34 configured to be connected to a proximal end of a catheter introducer (not shown). As generally known and understood in the art, the repositioning shield is easily axially compressible to allow balloon 14 and shaft 16 to be moved longitudinally relative to the catheter introducer.

FIG. 2 is a longitudinal cross-sectional view of balloon 14 of catheter 10 of FIG. 1. As shown in FIG. 2, shaft 16 includes an outer tube 36 and an inner tube 38, generally concentrically disposed through outer tube 36. Inner tube 38 includes a distal end 39. Outer tube 36 includes a distal end 40, which is sealably connected to the proximal end 15 of balloon 14. Inner tube 38 extends distally through outer tube 16 and balloon 14 to distal tip member 26. Inner tube 38 is preferably formed from a superelastic metal alloy, such as nitinol.

A gas lumen 42, in fluid communication with the inside of the balloon 14, is defined between outer tube 36 and inner tube 38. Inner tube 38 defines guidewire lumen 28 therethrough to distal tip member 26. Tip member 26 defines the remaining distal portion of guidewire lumen 28. The distal end 19 of balloon 14 is adhered to distal tip member 26 proximally. A strain relief 44 can be placed around inner tube 38, where tube 38 extends from distal tip member 26. Distal tip member 26 can include a marker band 46 to assist the physician in locating the distal tip of catheter 10 by radiological means.

FIG. 3 is a partial cross-sectional view of catheter 10 taken where shaft 16 and repositioning shield 30 are connected to hub 12. As shown in FIG. 3, outer tube 36 includes a proximal end 48 connected to hub 12 and extending distally therefrom. Inner tube 38 also includes a proximal end 50 connected to hub 12 and extending distally therefrom through outer tube 36. A typical guidewire 52 extends through guidewire lumen 28. Inner tube 38 defines most of guidewire lumen 28, however, the portion of guidewire lumen 28 extending between proximal end 50 of tube 38 and proximal end 24 of catheter 10 is defined by hub 12. Hub 12 also defines a portion of gas lumen 42 fluidly connecting that portion of gas lumen 42 defined by outer tube 36 and inner tube 38 with a lumen extending through gas tube 18. For clarity, strain relief 17 is not shown in FIG. 3.

The balloon 14 and outer tube 36 are preferably formed from polyurethane, and are preferably formed in one continuous piece having no adhesive joint at the proximal end of balloon 14. As well known in the art of balloon catheterization, numerous other materials may be used to form outer tube 38 and/or balloon 14. Also, balloon 14 need not be formed in one piece with outer tube 38. Distal tip member 26 is preferably formed from polyurethane, but may be formed from any other suitably biocompatible flexible material.

FIG. 4 is a partial elevational view of the intra-aortic balloon catheter 10 of FIG. 1, showing the inner tube 38. The inner tube 38 includes three regions, a high flexibility region A, a transition region B, and a low flexibility region C. The three zones of flexibility of inner tube 38 result in a high degree of pushability, while maintaining a more flexible tip.

In a preferred embodiment, the inner tube 38 is formed of nitinol, and the three regions of flexibility are defined by treatment of inner tube 38 in a high temperature salt bath. A nitinol tube having an austinite finish temperature of 19°–20° C. as starting material is first provided. A salt bath is then heated to a temperature in the range of 450° C. to 550° C. The nitinol tube is then immersed in the salt bath such that region A and B are submerged. The process of heating the nitinol tube raises its austinite finish temperature, and through a physical change in its material properties, the flexibility of the nitinol tube is increased. Since region C is not submerged it will retain its original austinite finish temperature of 19°–20° C. The tube is then extracted slowly at a selected rate from the salt bath until only region A remains submerged. This extraction time is typically in the range of 15–45 minutes. The nitinol tube is then removed from the salt bath after section A has achieved a selected austinite finish temperature. Although a molten salt bath is preferred, other means of heating the nitinol tube can be utilized.

There is an inverse relation ship between the necessary extraction time and the temperature of the salt bath. A higher temperature salt bath, for example, will require a shorter extraction time to reach the target austinite finish temperature. In this preferred embodiment, the final austinite finish temperature of region A is 30° C. Region C will have a constant austinite finish temperature of 20° C. Region B will have an austinite finish temperature that varies from 20° C. at the interface to region C, to 30° C. at the interface to region A. In this preferred embodiment, it is desirable that region A have a length that is approximately two inches, and that region B have a length of approximately 2 inches. In operation, balloon 14 preferably has a length of between 6–12 inches. It is understood, however, that regions A and B and balloon 14 can be varied.

In an alternative method of treatment, the entire nitinol tube is initially submerged in the salt bath to achieve a desired austinite finish temperature for region C. The tube is then removed, then reinserted and extracted slowly from the salt bath following the process described in the preferred embodiment above until only region A is submerged. The extraction time is determined by the desired austinite finish temperature for region A. The nitinol tube is then removed from the salt bath. It is understood in the alternative embodiment that the austinite finish temperature of region C, transition region B, or region A can be of any desired value as long as the austinite finish temperature of region A is greater than the austinite finish temperature of region C.

In another alternative method of treatment, the nitinol tube is extracted at a desired nonconstant rate in order to create a nonlinear transition region B. In this embodiment, transition region B will have a nonlinear variation in austinite finish temperature as a function of tube length.

In yet another alternative method, the nitinol tube is alternately held, then partially extracted at desired rates, thus creating any desired number of austinite finish temperature transition regions and constant temperature regions.

Numerous characteristics and advantages of the invention have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. In a catheter including a shaft having a proximal end, a distal end, and a balloon disposed proximate the distal end of the shaft, wherein the shaft includes an outer tube and inner tube disposed therethrough the improvement characterized by:

at least a portion of at least one of the tubes comprising nitinol, the nitinol portion having at least a first region of flexibility and a second region of flexibility along the longitudinal length thereof wherein the first region has a greater flexibility than the second region and a higher austenite finish temperature than the second region.

2. The catheter in accordance with claim 1, wherein the nitinol portion extends the entire longitudinal length of the tube.

3. The catheter in accordance with claim 2, wherein the austenite finish temperature of the first region is at least about 33 degrees C.

4. The catheter in accordance with claim 2, wherein the austenite finish temperature of the second region is at most about 20 degrees C.

5. The catheter in accordance with claim 2, wherein the first region is distal of the second region.

6. The catheter in accordance with claim 5, wherein the nitinol portion further comprises a third region of flexibility disposed longitudinally between the first and second regions of flexibility.

7. The catheter in accordance with claim 6, wherein the flexibility of the third region of flexibility has a distal end proximate the first region of flexibility and a proximal end proximate the second region of flexibility and the flexibility of the third region varies between the first and second regions of flexibility, the third region being most flexible proximate the distal end and least flexible proximate the proximal end.

8. The catheter in accordance with claim 7, wherein the austenite finish temperature of the third region varies between at least about 30 degrees C. proximate the distal end to at most about 20 degrees C. proximate the proximal end.

9. An intra-aortic balloon catheter, comprising:

a shaft having a proximal end and a distal end, the shaft including an outer tube and an inner tube disposed within the outer tube, wherein the inner tube defines a guide wire lumen therethrough and the inner tube and outer tube define an inflation lumen therebetween; and a balloon disposed at the distal end of the shaft, wherein the inflation lumen is in fluid communication with the interior of the balloon; wherein at least a portion of at least one of the tubes comprises nitinol, the nitinol portion having at least a first region of flexibility and a second region of flexibility along the longitudinal length thereof wherein the first region has a greater flexibility than the second region and a higher austenite finish temperature than the second region.

10. The catheter in accordance with claim 9, wherein the nitinol portion extends the entire longitudinal length of the tube.

11. The catheter in accordance with claim 10, wherein the austenite finish temperature of the first region is at least about 33 degrees C.

12. The catheter in accordance with claim 11, wherein the austenite finish temperature of the second region is at most about 20 degrees C.

13. The catheter in accordance with claim 12, wherein the first region is distal of the second region.

14. The catheter in accordance with claim 13, wherein the nitinol portion further comprises a third region of flexibility disposed longitudinally between the first and second regions of flexibility.

15. The catheter in accordance with claim 14, wherein the flexibility of the third region of flexibility has a distal end proximate the first region of flexibility and a proximal end proximate the second region of flexibility and the flexibility of the third region varies between the first and second regions of flexibility, the third region being most flexible proximate the distal end and least flexible proximate the proximal end.

16. The catheter in accordance with claim 15, wherein the austenite finish temperature of the third region varies between at least about 30 degrees C. proximate the distal end to at most about 20 degrees C. proximate the proximal end.

* * * * *